(12) United States Patent
Tanaka et al.

(10) Patent No.: US 8,173,806 B2
(45) Date of Patent: May 8, 2012

(54) METHOD FOR PRODUCTION OF QUINAZOLIN-4-ONE DERIVATIVE

(75) Inventors: Kazuo Tanaka, Niigata (JP); Yoshifumi Sato, Niigata (JP); Takafumi Yoshimura, Niigata (JP)

(73) Assignee: Mitsubishi Gas Chemical Company, Inc., Tokyo (JP)

( * ) Notice: Subject to any disclaimer, the term of this patent is extended or adjusted under 35 U.S.C. 154(b) by 871 days.

(21) Appl. No.: 12/282,381

(22) PCT Filed: Mar. 14, 2007

(86) PCT No.: PCT/JP2007/055096
§ 371 (c)(1),
(2), (4) Date: Sep. 10, 2008

(87) PCT Pub. No.: WO2007/011936
PCT Pub. Date: Oct. 25, 2007

(65) Prior Publication Data
US 2009/0054646 A1 Feb. 26, 2009

(30) Foreign Application Priority Data
Mar. 17, 2006 (JP) ................................. 2006-075162

(51) Int. Cl.
*C07D 239/72* (2006.01)
(52) U.S. Cl. ..................................................... 544/287
(58) Field of Classification Search .................. 544/287
See application file for complete search history.

(56) References Cited

U.S. PATENT DOCUMENTS

| | | | | |
|---|---|---|---|---|
| 4,490,557 | A | * | 12/1984 | Dawson et al. ............... 564/159 |
| 6,784,292 | B2 | * | 8/2004 | Winter et al. ................. 540/555 |
| 2005/0080262 | A1 | | 4/2005 | Nishino et al. |
| 2005/0124809 | A1 | | 6/2005 | Nishino et al. |

FOREIGN PATENT DOCUMENTS

| | | |
|---|---|---|
| JP | 2002-338550 | 11/2002 |
| WO | WO 96/09294 | 3/1996 |

OTHER PUBLICATIONS

Journal of Medicinal Chemistry, 32, 847-852, 850-851 (1989).*
F.W. Lichtenthaler, Heterocycles, 15(2) 1053-1058, 1058 (1981).*
B.R. Baker et al., Journal of Organic Chemistry, 141-148, 143 (1952).*
C.S. Harris et al, Tetrahedron Letters 46, 7381-7384 (2005).*
Seger et al., "Structure Elucidation and Synthesis of a New Bioactive Quinazolone Derivative Obtained from *Glycosmis Cf. Chlorospemal*", Chemical Pharmaceutical Bulletin, vol. 46, No. 12, pp. 1926-1928, Aug. 1998.

* cited by examiner

*Primary Examiner* — James O Wilson
*Assistant Examiner* — Alexander R Pagano
(74) *Attorney, Agent, or Firm* — Antonelli, Terry, Stout & Kraus, LLP.

(57) ABSTRACT

In reacting an anthranilic acid derivative represented by the general formula (1), especially the anthranilic acid derivative selected from anthranilic acid, anthranilamide and anthranilate, with formamide, the reaction is attained under the condition of coexistence of acetic acid and a base as a catalyst in the reaction liquid, and it has made it possible to produce a quinazolin-4-one derivative represented by the general formula (2) and useful as a material for medicine intermediates, at high yield with no side production.

4 Claims, No Drawings

METHOD FOR PRODUCTION OF QUINAZOLIN-4-ONE DERIVATIVE

TECHNICAL FIELD

The present invention relates to a method for producing a quinazolin-4-one derivative represented by a general formula (2).

Specifically, the present invention relates to a method for producing a quinazolin-4-one derivative represented by the general formula (2), comprising reacting an anthranilic acid represented by a general formula (1) with formamide in the presence of a catalyst.

A quinazolin-4-one derivative represented by the general formula (2) is an important compound as a material for medicine intermediates, etc.

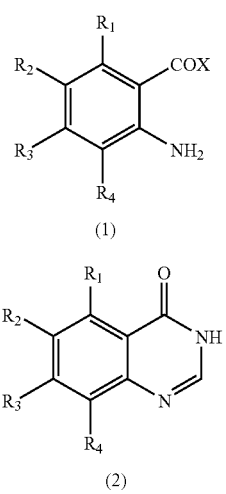

[Formula 1]

(1)

[Formula 2]

(2)

(In the formulae, $R_1$, $R_2$, $R_3$ and $R_4$ each independently represent a hydrogen atom, a halogen atom, a nitro group, or a $C_1$-$C_6$ alkyl or alkoxy group; X represents a hydroxyl group, an amino group, or a $C_1$-$C_6$ alkoxy group.)

BACKGROUND ART

Heretofore, for producing quinazolin-4-one derivatives from anthranilic acid derivatives, the following methods are known.

1) A method of producing 6-iodoquinazolin-4-one by reacting 5-iodoanthranilic acid and formamidine acetate under reflux in glacial acetic acid (for example, see Patent Reference 1); 2) a method of producing quinazolin-4-one by reacting ammonium formate and methyl anthranilate in the presence of formamide (for example, see Non-Patent Reference 1); 3) a method of producing quinazolin-4-one by reacting anthranilic acid and formamide in the absence of a catalyst (for example, see Non-Patent Reference 2); 4) a method of producing a quinazolin-4-one derivative by reacting an anthranilic acid derivative and an orthoformate in the presence of ammonia (for example, see Patent Reference 2); 5) a method of producing a quinazolin-4-one derivative by reacting an anthranilic acid derivative and an orthoformate in the presence of ammonium acetate (for example, see Patent Reference 3); 6) a method of producing a 6,7-dioxyquinazoline derivative by reacting a 4,5-dioxyanthranilate derivative and formamide, using formic acid or monobromoacetic acid as an acid catalyst or using an alkali metal carbonate as a basic catalyst (for example, see Patent Reference 4).

However, the method 1) of Patent Reference 1 has a problem in that expensive formamidine acetate must be used excessively as the nitrogen source and the carbon source for the quinazoline skeleton.

The method 2) of Non-Patent Reference 1 requires high-temperature and long-lasting reaction at 175° C. for 4 hours, and the yield of the obtained quinazolin-4-one is only at most 70%.

The method 3) of Non-Patent Reference 2 uses inexpensive formamide as the nitrogen source and the carbon source for the quinazoline skeleton; and the reaction with no catalyst at 130° C. for 2.5 hours gives an yield of 83. Thus, the production method is improved over the method of Non-Patent Reference 1, but the yield must be further enhanced in industrial application.

The method 4) of Patent Reference 2 uses ammonia as the nitrogen source, and uses an orthoformate as the carbon source.

According to the method, the reaction may be attained in the absence of a catalyst, but the method is problematic in that ammonia and further an expensive orthoformate must be used excessively.

The method 5) of Patent Reference 3 uses an ammonium carboxylate as the nitrogen source and uses an orthoformate as the carbon source, in which the reaction may be attained in the absence of a catalyst; however, the method is also problematic in that an expensive orthoformate must be used excessively therein.

The method 6) of Patent Reference 4 uses formamide as the nitrogen source and the carbon source for the quinazoline skeleton in producing a 6,7-dioxyquinazoline derivative; and using as a catalyst, an acid catalyst of formic acid or monobromoacetic acid or a basic catalyst of an alkali metal carbonate under a reaction temperature condition at 130° C., this produces a relatively good result of an yield of 90%; however, the reaction time is from 6 to 7 hours and is long, and this requires further improvement for industrial application.

As in the above, the conventional methods involve various problems that must be overcome, and are therefore not satisfactory.

[Patent Reference 1] JP-T 10-505600
[Patent Reference 2] JP-A 2003-183262
[Patent Reference 3] WO03/064399
[Patent Reference 4] JP-A 2002-338550
[Non-Patent Reference 1] B. R. BAKER, JOSEPH P. JOSEPH, ROBERT E. SCHAUB, FRANCIS J. McEVOY and JAMES H. WILLIAMS; J. Org. Chem., 18, 138 (1953)
[Non-Patent Reference 2] Christoph SEGER, Srunya VAJRODAYA, Harald GREGER, and Otmar HOFER; Chem. Pharm. Bull., 46(12) 1926-1928 (1998)

DISCLOSURE OF THE INVENTION

An object of the present invention is to provide a more efficient and industrially practicable method for producing a quinazolin-4-one derivative represented by the general formula (2), which is important as a material for medicines and others, from an anthranilic acid derivative represented by the genera formula (1) and formamide.

The present inventors have assiduously studied for the purpose of solving the above-mentioned problems, and have found that, when acetic acid and a base are made to coexist as a catalyst in the reaction solution, then a quinazolin-4-one derivative represented by the general formula (2) can be produced at a high yield within a short period of time under a mild reaction condition, and have reached the present invention.

Accordingly, the present invention relates to a highly-efficient and industrially-practicable method indicated in the following 1 to 5 for producing a quinazolin-4-one derivative represented by the general formula (2), from an anthranilic acid derivative represented by the general formula (1) and formamide.

Specifically, the present invention provides the following:

1. A method for producing a quinazolin-4-one derivative represented by a general formula (2) by reacting an anthranilic acid derivative represented by a general formula (1) and formamide, wherein the reaction is attained under the condition of coexistence of acetic acid and a base as a catalyst in the reaction liquid:

[Formula 3]

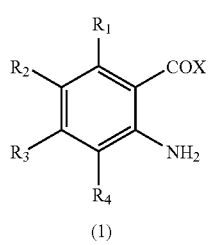

(1)

[Formula 4]

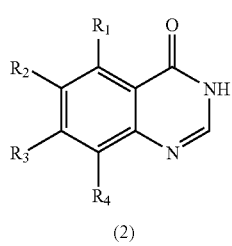

(2)

(wherein $R_1$, $R_2$, $R_3$ and $R_4$ each independently represent a hydrogen atom, a halogen atom, a nitro group, or a $C_1$-$C_6$ alkyl or alkoxy group; X represents a hydroxyl group, an amino group, or a $C_1$-$C_6$ alkoxy group);

2. The method for producing a quinazolin-4-one derivative represented by the general formula (2) of the above 1, wherein the amount of acetic acid and the base that coexist in the reaction liquid is both within a range of from 0.1 to 2.0 times by mol the anthranilic acid derivative represented by the general formula (1), and the molar ratio of the base to acetic acid is within a range of from 0.2 to 10 times by mol;

3. The method for producing a quinazolin-4-one derivative represented by the general formula (2) of the above 1, wherein the substance to be used for making acetic acid exist in the reaction liquid is at least one selected from acetic acid and a salt of acetic acid;

4. The method for producing a quinazolin-4-one derivative represented by the general formula (2) of the above 1, wherein the substance to be used for making the base exist in the reaction liquid is at least one selected from ammonia, lithium carbonate, sodium carbonate, potassium carbonate, cesium carbonate, sodium hydrogencarbonate, potassium hydrogencarbonate, cerium hydrogencarbonate, sodium methoxide, sodium ethoxide, potassium ethoxide, methylamine, ethylamine, propylamine, butylamine, dimethylamine, diethylamine, dipropylamine, ethylenediamine, propanediamine, trimethylamine and triethylamine;

5. The method for producing a quinazolin-4-one derivative represented by the general formula (2) of the above 3, wherein the salt of acetic acid is at least one selected from ammonium acetate, sodium acetate and potassium acetate.

BEST MODE FOR CARRYING OUT THE INVENTION

The method for producing a quinazolin-4-one derivative represented by the general formula (2) of the present invention is described in detail hereinunder.

The starting material, anthranilic acid derivative in the present invention is represented by the above-mentioned general formula (1).

In the general formula (1), $R_1$, $R_2$, $R_3$ and $R_4$ each independently represent a hydrogen atom, a halogen atom, a nitro group, or a $C_1$-$C_6$ alkyl or alkoxy group. X represents a hydroxyl group, an amino group, or a $C_1$-$C_6$ alkoxy group.

The halogen atom indicates a fluorine atom, a chlorine atom, a bromine atom or an iodine atom; and $R_1$, $R_2$, $R_3$ and $R_4$ may be all halogen atoms of the same time, or may be halogen atoms of different types.

The $C_1$-$C_6$ alkyl group means an alkyl group having from 1 to 6 carbon atoms, including a methyl group, an ethyl group, a propyl group, a butyl group, a pentyl group, a hexyl group. These groups include various isomers.

The $C_1$-$C_6$ alkoxy group means an alkoxy group having from 1 to 6 carbon atoms, including a methoxy group, an ethoxy group, a propoxy group, a butoxy group, a pentoxy group, a hexyloxy group.

These groups also include various isomers.

The anthranilic acid derivative represented by the general formula (1) is preferably anthranilic acid, anthranilamide or anthranilate represented by the general formula (1).

The anthranilic acid derivative represented by the general formula (1) may be a known compound, or may be produced according to a known method from a known compound, for example, by catalytic hydrogenation of a corresponding nitrobenzoic acid.

The nitrobenzoic acid may be produced, for example, according to the same method as in WO03/064399.

Formamide for use in the present invention may be an ordinary one commercially available as industrial materials or chemical reagents.

Not specifically defined, the amount of formamide to be used may be generally from 0.8 to 30 times by mol, preferably from 5 to 28 times by mol, more preferably from 10 to 25 times by mol, relative to one mol of the anthranilic acid derivative represented by the general formula (1).

When the amount of formamide to be used is less than 0.8 times by mol, then the base concentration may be thin and there may occur an inconvenience of reaction speed reduction.

On the other hand, when it is more than 30 times by mol, then much formamide must be recovered after the reaction and this is uneconomical.

The solvent for use in the present invention may be any one inert to the reaction, and its amount may be enough for always stirring the reaction mixture.

The usable solvent includes, for example, alcohols such as methanol, ethanol; esters such as methyl acetate, ethyl acetate; organic acids such as acetic acid; lactones such as butyrolactone; cyclic ethers such as tetrahydrofuran, dioxane; amides such as dimethylformamide, dimethylacetamide; lactams such as N-methylpyrrolidone; and ketones such as acetone, methyl isobutyl ketone, cyclohexanone. For the purpose of preventing the reaction system from being complicated, it is most desirable to use formamide itself as the solvent.

The reaction is attained under the condition of coexistence of acetic acid and a base, as a catalyst, in the reaction solution.

The substance to be used for making acetic acid exist in the reaction solution includes, for example, acetic acid and a salt of acetic acid to be an acetic acid source.

Preferred examples of the salt of acetic acid to be the acetic acid source are ammonium acetate, sodium acetate, potassium acetate.

Acetic acid and a salt of acetic acid to be the acetic acid source may be used singly or as combined.

The salt of acetic acid may be a single salt of acetic acid or a mixture of two or more different types of salts of acetic acid.

The amount of acetic acid to be in the reaction solution may be from 0.1 to 2.0 times by mol, preferably from 0.2 to 1.8 times by mol, more preferably from 0.4 to 1.6 times by mol, as the total amount of acetic acid and a salt of acetic acid to be the acetic acid source, relative to one mol of the anthranilic acid derivative represented by the general formula (1).

When the total amount of acetic acid and a salt of acetic acid to be the acetic acid source is less than 0.1 times by mol, then the conversion of the anthranilic acid derivative represented by the general formula (1) to the quinazolin-4-one derivative represented by the general formula (2) may lower, and the side production of a 2-formylanthranilic acid derivative through formulation of the 2-position amino group of the anthranilic acid derivative with formamide could not be ignored.

When the total amount of acetic acid and a salt of acetic acid to be the acetic acid source is more than 2.0 times by mol, then unidentified side products detectable in liquid chromatography may increase therefore bringing about an inconvenience of reduction in the quinazolin-4-one derivative selectivity.

The substance to be used for making a base exist in the reaction solution includes, for example, inorganic bases such as ammonia; alkali metal carbonates such as lithium carbonate, sodium carbonate, potassium carbonate, cesium carbonate; alkali metal hydrogencarbonates such as sodium hydrogencarbonate, potassium hydrogencarbonate, cesium hydrogencarbonate; alkali metal alkoxides such as sodium methoxide, sodium ethoxide, potassium ethoxide; organic amines such as methylamine, ethylamine, propylamine, butylamine, dimethylamine, diethylamine, dipropylamine, ethylenediamine, propanediamine, trimethylamine, triethylamine.

Of those, preferred are inorganic bases such as ammonia and organic amines such as propylamine, diethylamine, ethylenediamine; and more preferred is ammonia in view of its convenience.

One or more of these bases may be used either singly or as combined.

The amount of the base to be in the reaction solution may be from 0.1 to 2.0 times by mol, preferably from 0.2 to 1.8 times by mol, more preferably from 0.4 to 1.6 times by mol, relative to 1 mol of the anthranilic acid derivative of the general formula (1).

When the amount of the base falls within the above range, then it is effective for inhibiting the side production of 2-formylanthranilic acid derivatives.

As in the above, the present invention comprises use of acetic acid and a base to coexist as a catalyst in the reaction solution in producing a quinazolin-4-one derivative represented by the general formula (2) by reaction of an anthranilic acid derivative represented by the general formula (1) and formamide.

The ratio of the base to acetic acid to be in the reaction solution may be from 0.05 to 20 times by mol, preferably from 0.1 to 20 times by mol, more preferably from 0.2 to 10 times by mol, even more preferably from 0.3 to 5 times by mol.

Coexistence of acetic acid and a base as a catalyst in the reaction solution enables the reaction at a mild temperature within a short period of time.

The reaction of the present invention may be attained, for example, according to a method of mixing and stirring an anthranilic acid derivative represented by the general formula (1) and formamide, together with a catalyst comprising acetic acid and a base in an inert gas atmosphere.

The reaction temperature may be from 100 to 170° C., preferably from 110 to 160° C., more preferably from 120 to 155° C.

When the reaction temperature is lower than 100° C. or higher than 170° C., then side reactions may increase.

Specifically, at lower than 100° C., the side production of 2-formylanthranilic acid derivatives through formulation of the anthranilic acid derivative may increase; and at higher than 170° C., unidentified side products detectable in liquid chromatography may increase, therefore lowering the selectivity of the quinazolin-4-one derivative represented by the general formula (2).

Coexistence of acetic acid and a base as a catalyst in the reaction solution may prevent the formation of side products such as 2-formylanthranilic acid derivatives, and therefore the intended quinazolin-4-one derivative represented by the general formula (2) can be produced at high conversion and high selectivity.

The reaction time may be generally from 0.5 to 10 hours, preferably from 1 to 5 hours.

The reaction pressure may be a pressure capable of maintaining a liquid phase, generally normal pressure.

After the reaction, the reaction mixture may be crystallized, for example, by cooling it to room temperature.

The crystallized precipitate is collected by filtration, and further the collected cake is washed, for example, with a solvent of the same composition as that used in the reaction, and thereafter dried in vacuum to give a white crystal of the intended quinazolin-4-one derivative represented by the general formula (2).

In case where the product requires further purification depending on its use and object, it may be purified according to an ordinary method of recrystallization, fractional distillation, fractional chromatography, etc.

EXAMPLES

The present invention is described more concretely with reference to the following Examples and Comparative Examples.

However, the present invention should not be limited by these Examples.

Example 1

Production of 6,7-dimethoxyquinazolin-4-one

Using acetic acid and an inorganic base, ammonia, as a catalyst, 6,7-dimethoxyquinazolin-4-one was produced in the manner mentioned below.

0.84 g (4 mmol) of methyl 4,5-dimethoxyanthranilate, 3.60 g (80 mmol) of formamide, 0.17 g (2.8 mmol) of acetic acid and 0.05 g (2.8 mmol) of ammonia from a pressure cylinder were put into an autoclave of SUS316 having a capacity of 25 mL and equipped with a stirrer, a thermometer and a pressure gauge in a nitrogen atmosphere, and reacted at 150° C. for 2 hours.

After the reaction, the reaction liquid was cooled to room temperature, and the precipitated crystal was collected by filtration, washed with methanol and then dried in vacuum at 70° C. for 2 hours to obtain 0.77 g of a crystal.

The obtained crystal was analyzed for the purity by high-performance liquid chromatography, and its purity was 99.5%; and 6,7-dimethoxyquinazolin-4-one was obtained at a yield of 93.0%.

The result is shown in Table 1.

Examples 2 to 4, and Comparative Examples 1 and 2

Production of 6,7-dimethoxyquinazolin-4-one

The reaction and the post-treatment were carried out in the same manner as in Example 1, for which, however, the catalyst was changed as in Table 1.

In Example 4, ammonium acetate was used as the catalyst; and in Comparative Examples 1 and 2, formic acid or potassium carbonate, respectively, was used alone as the catalyst like in JP-A 2002-338550 (Patent Reference 4).

From the results in Table 1, it is known that the reaction system with acetic acid and a base coexisting therein of the present invention gives 6,7-dimethoxyquinazolin-4-one at a higher yield than the conventional reaction system with formic acid or potassium carbonate alone therein.

TABLE 1

| | Catalyst | Yield of 6,7-Dimethoxyquinazolin-4-one (%) |
|---|---|---|
| Example 1 | acetic acid/ammonia | 93.0 |
| Example 2 | acetic acid/diethylamine | 88.8 |
| Example 3 | acetic acid/ethylenediamine | 87.5 |
| Example 4 | ammonium acetate | 92.1 |
| Comparative Example 1 | formic acid | 67.5 |
| Comparative Example 2 | potassium carbonate | 36.4 |

Example 5

Production of 6-iodoquinazolin-4-one

With acetic acid and a base coexisting as a catalyst in the reaction system, 6-iodoquinazolin-4-one was produced in the manner mentioned below.

1.05 g (4 mmol) of 5-iodoanthranilic acid, 3.60 g (80 mmol) of formamide, 0.17 g (2.8 mmol) of acetic acid and 0.17 g (2.8 mmol) of diethylamine were put into an autoclave of SUS316 having a capacity of 25 mL and equipped with a stirrer, a thermometer and a pressure gauge in a nitrogen atmosphere, and reacted at 150° C. for 2 hours.

After the reaction, the reaction liquid was cooled to room temperature, and the precipitated crystal was collected by filtration, washed with acetic acid and then dried in vacuum at 70° C. for 2 hours to obtain 1.01 g of a crystal.

The above mother liquid was 3.98 g.

The obtained crystal and the mother liquid were analyzed for the purity by high-performance liquid chromatography using 5-iodo-2-methylbenzoic acid as an internal standard substance; and the purity of the crystal was 99.5%, 6-iodoquinazolin-4-one in the mother liquid was a trace, and the yield of 6-iodoquinazolin-4-one was 92.3%.

The result is shown in Table 2 and Table 3.

Examples 6 to 9, and Comparative Examples 3 to 5

Production of 6-iodoquinazolin-4-one

The reaction and the post-treatment were carried out in the same manner as in Example 5, for which, however, the catalyst was changed.

Comparative Examples demonstrate a case with no catalyst, a case with an acid catalyst alone, and a case of a base catalyst alone.

The results are shown in Table 2.

TABLE 2

| | Catalyst | Yield of 6-Iodoquinazolin-4-one (%) |
|---|---|---|
| Example 5 | acetic acid/diethylamine | 92.3 |
| Example 6 | acetic acid/isopropylamine | 90.2 |
| Example 7 | acetic acid/ethylenediamine | 93.0 |
| Example 8 | sodium acetate | 89.9 |
| Example 9 | ammonium acetate | 93.0 |
| Comparative Example 3 | no catalyst | 75.0 |
| Comparative Example 4 | formic acid | 82.0 |
| Comparative Example 5 | potassium carbonate | 81.0 |

Examples 10 to 12, and Comparative Examples 6 and 7

Production of 6-iodoquinazolin-4-one

The reaction and the post-treatment were carried out in the same manner as in Example 5, for which, however, the amount of acetic acid or the amount of diethylamine (DEA) relative to 5-iodoanthranilic acid (IAAc) was changed.

Comparative Examples demonstrate a case with acetic acid (2.8 mmol) alone and a case with diethylamine (2.8 mmol) alone.

The results are shown in Table 3 including Example 5.

TABLE 3

DEA: diethylamine, IAAC: 5-iodoanthranilic acid

| | DEA/IAAc, by mol | acetic acid/ IAAc, by mol | Yield of 6-Iodoquinazolin-4-one (%) |
|---|---|---|---|
| Example 10 | 0.7 | 1.4 | 90.1 |
| Example 5 | 0.7 | 0.7 | 92.3 |
| Example 11 | 0.7 | 0.35 | 93.4 |
| Example 12 | 1.4 | 0.35 | 91.2 |
| Comparative Example 6 | 0 | 0.7 | 85.1 |
| Comparative Example 7 | 0.7 | 0 | 86.1 |

From Table 3, it is known that the coexistence of acetic acid and dimethylamine as a catalyst in the reaction system increases the yield of 6-iodoquinazolin-4-one, as compared with the case of using acetic acid alone or diethylamine alone as the catalyst.

Examples 13 to 21

The reaction and the post-treatment were carried out in the same manner as in Example 5, for which, however, the type of the anthranilic acid derivative was changed.

The results are shown in Table 4.

TABLE 4

| | Anthranilic Acid Derivative | Quinazolin-4-one Derivative | Yield (%) |
|---|---|---|---|
| Example 13 | anthranilic acid | quinazolin-4-one | 93.8 |
| Example 14 | 4-chloroanthranilic acid | 7-chloroquinazolin-4-one | 96.1 |
| Example 15 | 5-chloroanthranilic acid | 6-chloroquinazolin-4-one | 93.3 |
| Example 16 | 5-fluoroanthranilic acid | 6-fluoroquinazolin-4-one | 85.0 |
| Example 17 | methyl anthranilate | quinazolin-4-one | 89.1 |
| Example 18 | anthranilamide | quinazolin-4-one | 96.0 |
| Example 19 | methyl 4-chloroanthranilate | 7-chloroquinazolin-4-one | 84.1 |
| Example 20 | methyl 5-chloroanthranilate | 6-chloroquinazolin-4-one | 94.1 |
| Example 21 | methyl 5-iodoanthranilate | 6-iodoquinazolin-4-one | 87.1 |

INDUSTRIAL APPLICABILITY

The present invention provides an economical method for producing a quinazolin-4-one derivative represented by the general formula (2) and useful as a material for medicine intermediates, etc.

The invention claimed is:

1. A method for producing a quinazolin-4-one derivative represented by a general formula (2) by reacting an anthranilic acid derivative represented by a general formula (1) and formamide, wherein the reaction is attained under the condition of coexistence of acetic acid and a base as a catalyst in the reaction liquid:

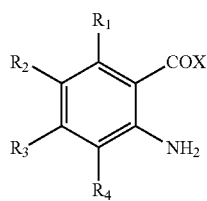

(1)

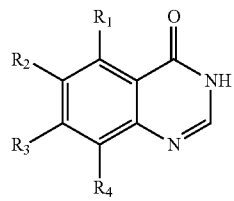

(2)

(wherein R1, R2, R3 and R4 each independently represent a hydrogen atom, a halogen atom, a nitro group, or a C1-C6 alkyl or alkoxy group; X represents a hydroxyl group, an amino group, or a C1-C6 alkoxy group), and wherein an amount of acetic acid in the reaction liquid is within a range of from 0.1 to 2.0 times by mol the anthranilic acid derivative represented by the general formula (1), the amount of the base in the reaction liquid is within a range of from 0.1 to 2.0 times by mol the anthranilic acid derivative represented by the general formula (1), and the molar ratio of the base to acetic acid is within a range of from 0.2 to 10 times by mol.

2. The method for producing a quinazolin-4-one derivative represented by the general formula (2) as claimed in claim 1, wherein a substance to be used for making acetic acid exist in the reaction liquid is at least one selected from acetic acid and a salt of acetic acid.

3. The method for producing a quinazolin-4-one derivative represented by the general formula (2) as claimed in claim 1, wherein a substance to be used for making the base exist in the reaction liquid is at least one selected from ammonia, lithium carbonate, sodium carbonate, potassium carbonate, cesium carbonate, sodium hydrogencarbonate, potassium hydrogencarbonate, cerium hydrogencarbonate, sodium methoxide, sodium ethoxide, potassium ethoxide, methylamine, ethylamine, propylamine, butylamine, dimethylamine, diethylamine, dipropylamine, ethylenediamine, propanediamine, trimethylamine and triethylamine.

4. The method for producing a quinazolin-4-one derivative represented by the general formula (2) as claimed in claim 2, wherein the salt of acetic acid is at least one selected from ammonium acetate, sodium acetate and potassium acetate.

* * * * *